United States Patent [19]

Trundle

[11] Patent Number: 4,942,113

[45] Date of Patent: Jul. 17, 1990

[54] CONTRAST ENHANCED PHOTOLITHOGRAPHY

[75] Inventor: Clive Trundle, Silverstone, England

[73] Assignee: Plessey Overseas Limited, Essex, England

[21] Appl. No.: 319,249

[22] Filed: Mar. 6, 1989

Related U.S. Application Data

[63] Continuation of Ser. No. 30,414, Mar. 27, 1987, abandoned.

[30] Foreign Application Priority Data

Mar. 27, 1986 [GB] United Kingdom ............... 8607715
Jun. 3, 1986 [GB] United Kingdom ............... 8613420

[51] Int. Cl.$^5$ .............................................. G03C 5/00
[52] U.S. Cl. ................................. 430/326; 430/271;
430/273; 430/325; 430/327; 430/292; 430/312;
430/339; 430/343; 430/396
[58] Field of Search .............. 430/312, 339, 292, 271,
430/273, 325, 326, 327, 333, 334, 343, 396

[56] References Cited

U.S. PATENT DOCUMENTS

| 4,663,275 | 5/1987 | West et al. .................. 430/339 |
| 4,702,996 | 10/1987 | Griffing et al. ................ 430/339 |

FOREIGN PATENT DOCUMENTS

| 0140540A2 | 3/1985 | European Pat. Off. . |
| 8300568 | 2/1983 | PCT Int'l Appl. . |
| 1294175 | 10/1972 | United Kingdom . |
| 1464603 | 2/1977 | United Kingdom . |

OTHER PUBLICATIONS

G. H. Brown, "Techniques of Chemistry", vol. III, Photochromism, 1971, pp. 594–597 and 740–745.
Wiley Series on Photographic Science, etc. edited by Walter Clark, "Light–Sensitive Systems", Section by Jaromir Kosar, Wiley, 1974, pp. 380–383, 392–394, 396 and 397.
Solid State Technology, vol. 28, No. 5, May 1985, pp. 152–157, article by B. F. Griffing et al. entitled "Contrast Enhanced Lithography".
P. R. West et al, "Contrast Enhanced Photolithography: Application of Photobleaching Processes in Microlithography", Jour. of Imaging Science, vol. 30, Mar./Apr. 1986, pp. 65–68.

*Primary Examiner*—Jack P. Brammer
*Attorney, Agent, or Firm*—Sughrue, Mion, Zinn, Macpeak & Seas

[57] ABSTRACT

The contrast and sharpness of photoresist images is enhanced by depositing a layer of a photobleachable compound onto the photoresist layer. The photobleachable layer is sensitive to the light used to expose the photoresist and forms a contrast enhancement layer (CEL) on the photoresist layer. Fulgides and photochromic butyrolactones are selected for forming the photobleachable layer. Such compounds can be deposited from a hydrocarbon solution, such as toluene, and are soluble in the standard alkali, photoresist developers. The process is particularly advantageous for producing integrated circuits.

18 Claims, No Drawings

CONTRAST ENHANCED PHOTOLITHOGRAPHY

This is a continuation of application Ser. No. 030,414 filed Mar. 27, 1987, now abandoned.

This invention relates to photolithography and in particular provides a means for producing photoresists having improved resolution.

BACKGROUND OF THE INVENTION

Electronic integrated circuits are routinely produced by photolithography using a photoresist coated onto a semi-conductor wafer. In such processes the wafer is coated with a layer of the photoresist which is then subjected to a soft bake (e.g. at about 90° to 100° C.) to remove the solvent. The prepared photoresist is then exposed through an imaging negative to form the desired circuit pattern on the surface of the photoresist and then developed to produce a replica of the circuit pattern in the developed resist.

Imaging of positive photoresists is carried out by various optical systems including both contact printers and projection equipment. The demand for greater miniaturisation of circuits increases the problems of resolving finer and finer image lines in photoresists. The maximum possible resolution of fine detail obtainable depends both on the quality of the optical system and on the ability of the photoresist materials to reproduce, in sharp relief, such fine detail. In the present state of the art, the limiting factor is the ability of the developed photoresists to reproduce the desired pattern. This arises because of the difficulty of maintaining sufficient contrast between fine lines in the pattern for a sharp image to be reproduced. As contrast falls with decreasing line width, discrimination of darker areas in a pattern from lighter areas becomes increasingly difficult. On development of the resulting exposed photoresists, wall angles of the pattern depart more and more from the vertical, thus representing poorer definition. If a satisfactory way can be provided for enhancing the contrast, finer detail can be reproduced more sharply without any requirement for corresponding improvements in the optical system.

Contrast enhancement can be achieved by coating the incident surface of the photoresist with a layer of material which is opaque but is bleachable by the radiation employed to expose the photoresist. As a consequence, an in situ mask is formed on the surface of the photoresist, the pattern of which corresponds to that of the imaging negative and this mask has the effect of amplifying the contrast between light and dark areas.

For example, U.K. Patent Specification No. 2131190 (General Electric) describes a process for producing integrated circuits which utilise such a contrast enhancement technique. However, the contrast enhancement layer in the General Electric process cannot be removed using the photoresist developer but necessitates a separate removal step. Furthermore, the photochromic compounds described in the above General Electric patent specification have practical disadvantages, such as sensitivity to water and a tendency to undergo fatigue reactions when stored in solution. Also, the polymer solutions of photochromic compounds employed to form the contrast enhancement layer develop a tacky surface which prevents their use in contact lithography.

U.K. patent specification Nos. 513029 (Kalle), describes a diazotype reflex copying process in which two, similar light-sensitised transparent sheets are placed in contact and together exposed to a light pattern of an original. However, there is no disclosure of any use of the copying process to prepare photoresists.

U.K. patent specification No. 1294105 (Kalle), is concerned with the production of planographic printing formes. A planographic forme is produced by coating an aluminium plate with a first light sensitive layer and applying a second layer or film to the first layer. The second layer or film contains a light-absorbing chemical which captures more of the incident light on image-wise exposure of the coated plate than would the light sensitive layer alone.

SUMMARY OF THE INVENTION

According to one aspect of the present invention there is provided a process for producing a developed photoresist having improved resolution by photolithography which comprises forming a photoresist layer on a substrate, applying a contrast enhancing layer (CEL) to the photoresist layer, said CEL comprising a solution or dispersion of a photobleachable, coloured compound in a solvent and heating the layer to drive off the solvent, exposing the photoresist through an imaging pattern and through the CEL using radiation which is effective to bleach said compound and removing the CEL and simultaneously developing the photoresist using a developer in which exposed areas of the photoresist and the CEL are both soluble.

Other features and advantages of the present invention will become apparent from the following detailed description.

DETAILED DESCRIPTION OF THE INVENTION

A number of positive photolithographic resists utilise an alkali based developer which is conveniently used to remove the CEL material in the developing step.

The CEL materials which are used in the process of the present invention may be generally described as reversible photochromic compounds which are derivatives of a succinic anhydride, a succinimide or a succinic ester. Typical photochromic materials are fulgides and fulgimides which are converted to their coloured form by heating to a temperature of about 100° C. or irradiation with UV light or by a combination of both treatments. Such compounds are rapidly bleached with white light, their maximum absorbance being generally in the range of 400 to 550 nm. Compounds having absorbance maxima at or close to 400 nm are preferred, since many conventional photoresist materials are designed for exposure to illuminating radiation in this part of the visible spectrum.

Suitable photochromic materials may be represented by the general formula (I) below:

(1)

wherein Y represents

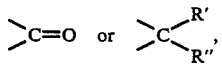

R' and R" being hydrogen or alkyl,
X represents oxygen or

in which A is hydrogen or an alkyl group or aryl group, $R_1$, $R_2$, $R_3$ and $R_4$ represent aryl, alkyl, aralkyl, hydrogen or heterocyclic groups.

Typical examples of suitable fulgides or fulgimides (and their preparation) are described in British Patents Nos. 1,442,628, 1,464,603, 2,002,752 and U.S. Pat. Nos. 4,186,002, 4,145,536 and 4,220,708 the disclosure of which is specifically incorporated herein. As described in these British and U.S. patents, these fulgides and fulgimides are converted into their cyclised coloured form by heating to about 100° C. or irradiation with U.V. light or by a combination of both.

Generally the compounds of formula (I) above in which X represents an imide group have absorbance maxima in the shorter wavelength and may be preferred for use with some photoresist materials.

It is also possible to use the succinic acid esters and half esters corresponding to the above described succinic anhydride compounds.

A preferred group of reversibly photochromic compounds have the general formula (2):

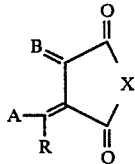

(2)

wherein
X represents oxygen or

in which A is hydrogen, or an alkyl or aryl group,

R represents an alkyl, aryl, aralkyl or heterocyclic group,

A represents a furyl, thienyl, benzofuryl or benzothienyl group,

B represents an adamantylidene group or the grouping

wherein
$R_6$ and $R_7$ independently represent an alkyl, aryl, aralkyl or heterocyclic group or one of $R_6$ and $R_7$ represent hydrogen and the other represents an alkyl, aryl, aralkyl or heterocyclic group.

Included within the general formula (I) above and having usefulness in the present invention is a series of photochromic gamma butyrolactones having the general formula (3):

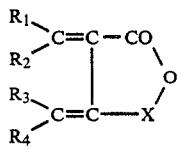

(3)

in which X represents

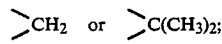

$R_1$, $R_2$ and $R_4$ independently represent a group selected from hydrogen, alkyl or aryl (including substituted aryl), with the proviso that one of $R_1$ and $R_2$ is always hydrogen, and $R_3$ is a 3-thienyl, 3-furyl, 3-benzothienyl or 3-benzofuryl group in which the 2-position is substituted with an alkyl, aralkyl or aryl group (including substituted aryl,).

These γ-butyrolactones are novel compounds and are advantageously used in the process of the present invention since they exhibit absorbance maxima at shorter wavelengths than the corresponding fulgides In the above formula (3), the aryl group or groups is preferably phenyl or alkyl substituted phenyl and the alkyl group(s) is preferably lower alkyl (e.g. methyl, ethyl, propyl or butyl).

Lactones compounds of the general formula (3) have the ability to undergo reversible ring closure to a coloured form, the ring closure being induced either thermally or by irradiation with light in the U.V. region or by a combination of both heating and irradiation. Heating alone to temperatures in the region of 100° C. will generally bring about ring closure. The coloured form can be produced by irradiation with U.V. light at lower temperatures, e.g. ambient.

The formation of the coloured state is illustrated by the following equation which shows the photocyclisation of a 3-thienyl or 3-furyl butyrolactone:

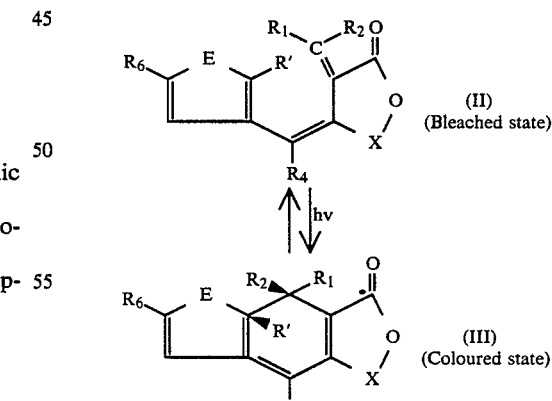

In the above formulae (II) and (III), $R_1$, $R_2$, $R^1$, $R_4$, $R_6$ and X have the same significance as in formula (I) and E represents oxygen or sulphur The thermally or U.V. induced ring closure occurs by ring closure onto the 2-position of the thienyl or furyl ring and does not involve the formation of radicals or reactive intermediates. Reversal is effected by irradiation with light at about 440 nm wavelength. Typically, the coloured compounds are bleached by irradiation with a laser of 436 nm wavelength. The compounds of the invention are very resistant to fatigue reactions leading to formation of irreversible products. This is achieved by blocking the only significant fatigue process, a 1,5 hydrogen shift, by introducing a nonhydrogen substituent $R^1$ in the 2-position. As a consequence, there is a virtual absence of fatigue reactions and the compounds are capable of undergoing a very large number of colour change cycles.

The coloured form of compounds of this invention are generally yellow to red, the precise absorption characteristics depending on the substituents in the furan or thiophene ring or whether this is benzannelated.

Compounds in which one of $R_1$ and $R_2$ is hydrogen have the advantage that ring closure can be effected by heating, generally to a temperature of about 100° C. or less. For example, such compounds can be converted to their coloured form by heating in refluxing toluene. In this manner, substantially 100% of the lactone is converted to the coloured form, whereas irradiation with U.V. light generally achieves a maximum of about 60% conversion. This property is of particular value in the contrast enhancement of photolithographic images. A coloured layer of a lactone of the above general formula can be coated onto a photoresist and exposed through an imaging negative using light of a wavelength which bleaches the coloured form of the lactone.

The lactones of general formula (3) can be prepared in a first stage by condensing a ketone of formula (IV) below with a diester of a succinic acid of formula (V) below using a Stobbe condensation:

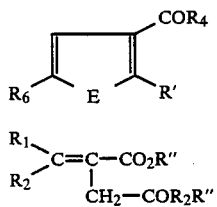

$$R_1 \atop R_2 \Big> C=C-CO_2R'' \atop \phantom{C=}CH_2-COR_2R''$$ (V)

where R' is an alkyl residue, such as ethyl.

In the next stage of the synthesis, the resultant acid ester is reduced to an acid alcohol by a suitable reducing agent, e.g. Super hydride (lithium triethylborohydride) or methyl lithium, followed by dehydration to yield the lactone The following Preparation illustrates the preparation of lactones in accordance with the invention.

Preparation

2-Methyl-3-acetyl-5-phenylfuran (40 g) and diethyl E-benzylidene succinate (55 g) in toluene was added dropwise to a suspension of sodium hydride (50% suspension in oil) (20 g) in toluene. The reaction was maintained at room temperature and stirred for 12 hours. The resultant solution was poured onto ice and the sodium salt of the acid ester extracted with water. The aqueous extract was acidified (5M HCl) and extracted with ether. The ether layer was dried and evaporated to give crude acid ester (30 g).

To acid ester (8 grms) in tetrahydrofuran was added superhydride (100 cm³ 0.1M solution in THF) and the solution refluxed (8 hours) and left to cool overnight. The solution obtained was poured onto ice and the THF evaporated. The residue was acidified with iced HCl and extracted with ether. The ethereal solution of acid alcohol was dehydrated by heating with p-toluene sulphonic acid and the lactone (2 g) separated from the reaction mixture by chromatography (alumina (neutral)/chloroform).

The photochromic compounds described above have the advantage that they are stable when stored in solution in the dark at ambient temperature for several months and are not sensitive to degradation in the presence of water. They can be conveniently coated onto the surface of a photoresist and stripped from the photoresist at the same time as development since they are soluble in the alkaline developing materials used for developing conventional photoresists.

Many of the fulgides described above are stable to the temperatures at which photoresists are baked and are converted into their coloured form at normal baking temperatures. Thus, the contrast enhancement layers can be applied to the photoresist by conventional spin casting procedures, and baked to remove the solvent at a temperature and for a time sufficient to convert the photochromic material to its coloured form.

In the practice of this invention, a semi-conductor wafer, such as a silicon wafer, or other substrate, such as lithium niobate is coated with a photoresist layer by spin-coating. Examples of positive photoresists which may be employed include photosensitive polyimide prepolymers and low molecular weight novalac resins. These can be developed using alkaline developing solutions.

Although the invention has been described largely in connection with contrast enhancement lithography using positive photoresists, the invention can also be applied to negative photoresists. One example of such a resist is a resist based on bis aryl azide and a polyisoprene. The aryl azide causes cross-linking of the rubber under the influence of light and the unexposed areas are removed during development with a solvent such as toluene or xylene in which the CEL is also soluble.

Examples of patent literature describing photoresist preparations include U.S. Pat. Nos. 4123272; 3169868; 3143423; 3046120; 3201239 and 2610120.

DETAILED DESCRIPTION OF THE PREFERRED EMBODIMENTS

EXAMPLE

A photoresist layer was formed on a silicon semiconductor layer by spin-coating with a conventional positive photoresist, such as a thinned novalak-type phenolformaldehyde resin composition diluted with 2-ethoxyethyl acetate and containing a photosensitive crosslinking agent as marketed by The Shipley Company under the trade name AZ111. A rotation speed is selected which, coupled with the viscosity of the resist composition, will give a final coating thickness of from about 1 to 2 microns.

A 1% solution of 2,5-dimethyl-3-furylethylidene (benzylidene) succinic anhydride (which is the photochromic succinic anhydride derivative of the general formula (2) in which X is oxygen, R is methyl, A is 2,5-dimethyl-3-furyl and B is benzylidene) was then prepared and filtered to remove particles greater than about 0.2 microns. We have found that a 1 to 5% solution of the photochromic compound in toluene or xylene is generally suitable. The solution of the photochromic compound was is then spin-coated onto the resist at a speed such as to produce a layer having a thickness of between about 0.3 to 1 micron after drying. The resultant coated photoresist is then heated to remove solvent and to give a soft bake to the photoresist. Care was taken to avoid baking the resist for too long; otherwise the photosensitivity of the photoresist is lost. A microcircuit pattern is then formed on the resulting multi-layer structure by exposing the structure to the appropriate illuminating radiation through a transparent, imaging screen (negative). The illuminating radiation is of a wavelength to which the photoresist is sensitive and at which the photochromic material is rapidly bleached. Normally, substantially monochromatic light having a wavelength in the 400 to 500 nm range is employed, but could be as low as 360 nm depending on the absorption spectra of the selected photochromic compound. In the case of the particular photochromic compound used in this Example, the illuminating radiation had a wavelength of 436 nm. After exposure the CEL coated photoresist is developed with an alkaline stripper e.g. aqueous ammonium hydroxide or an amine developer, which removes the CEL and the unexposed portions of the photoresist simultaneously. It is a surprising feature of the process of the invention that CEL layers only about 0.5 micron thick formed from the photochromic fulgides described above contribute a substantial enhancement to the degree of resolution of fine lines in a microelectronic circuit. Reproduction of detail containing lines separated by less than about one micron has been achieved with resist walls substantially vertical compared with resist wall angles of the order of 80° using the same projection equipment but without the CEL. The resulting silicon wafer having a developed photoresist pattern can be used to fabricate a microelectronic integrated circuit by a conventional Procedure, e.g. that described in U.S. Pat. No. 3873361.

The Example was repeated with the same result using as the photochromic compound a gamma butyrolactone obtained in the above Preparation, which has the general formula (3) above in which $R_1$ is hydrogen, $R_2$ is methyl, $R_3$ is 5-phenyl-2-methyl-3-furyl and $R_4$ is methyl.

The CEL may be deposited from a solution or dispersion which also contains a low molecular weight resin (such as a novolac resin having a molecular weight from about 700 to 1000) which is soluble in the photoresist developer. Also as an alternative to the aromatic hydrocarbon solvents mentioned above in the Example, one may use higher alcohols and esters, such as 2-ethoxy ethanol and 2-ethoxyethyl acetate. Advantageously, solvents are selected in which both the photochromic compound and the photoresist resin are soluble.

I claim:

1. A process for producing a developed photoresist having improved resolution by photolithography which comprises the steps of:
   (a) forming a photoresist layer on a substrate,
   (b) forming a contrast enhancing layer (CEL) directly on the photoresist layer by applying to said photoresist layer a solution or dispersion of a photobleachable, coloured compound in a solvent, followed by heating to form a dry, non-attack superficial layer of a CEL in direct contact with said photoresist, said coloured compound being present in a sufficient amount to render the superficial layer opaque,
   (c) exposing the photoresist through an imaging pattern and through the CEL using radiation which is effective to bleach said compound, and
   (d) simultaneously removing the CEL and developing the photoresist using a single developer in which both the CEL and the photoresist are soluble, said photobleachable, coloured compound being selected from a reversible photochromic compound having the general formula (1):

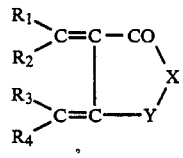

(1)

wherein Y represents

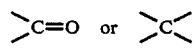

R' and R" being hydrogen or alkyl,
X represents oxygen or

in which A is hydrogen or an alkyl or aryl group, and
$R_1$, $R_2$, $R_3$ and $R_4$ represent aryl, alkyl, aralkyl, hydrogen or heterocyclic groups.

2. A process for producing a developed photoresist having improved resolution by photolithography which comprises the steps of:
   (a) forming a positive photoresist layer on a substrate,
   (b) applying a contrast enhancing layer (CEL) directly on the photoresist layer by applying to said photoresist layer a solution or dispersion of a photobleachable compound in a solvent followed by drying to produce a superficial layer of a CEL in direct contact with said photoresist, said coloured compound being present in a sufficient amount to render the superficial layer opaque,
   (c) exposing the photoresist through an imaging pattern and through the CEL using radiation which is effective to bleach said compound and
   (d) simultaneously removing the CEL and developing the photoresist using an aqueous alkali developer, wherein the photobleachable compound is selected from compounds of the general formula (2):

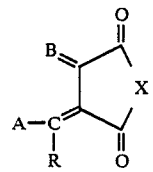

(2)

wherein
X represents oxygen or

in which A is hydrogen or an alkyl or aryl group,
R represents an alkyl, aryl, aralkyl or heterocyclic group,
A represents a furyl, thienyl, benzofuryl or benzothienyl group, and
B represents an adamantylidene group or the grouping

wherein $R_6$ and $R_7$ independently represent an alkyl, aryl, aralkyl or heterocyclic group or one of $R_6$ and $R_7$ represent hydrogen and the other represents an alkyl, aryl, aralkyl or heterocyclic group.

3. A process for producing a developed photoresist having improved resolution by photolithography which comprises the steps of:
 (a) forming a photoresist layer on a substrate,
 (b) applying a contrast enhancing layer (CEL) directly on the photoresist layer by applying to said photoresist layer a solution or dispersion of a photobleachable compound in a solvent, followed by drying to produce a superficial layer of a CEL in direct contact with said photoresist, said coloured compound being present in a sufficient amount to render the superficial layer opaque,
 (c) exposing the photoresist through an imaging pattern and through the CEL using radiation which is effective to bleach said compound, and
 (d) simultaneously removing the CEL and developing the photoresist using an alkali developer, wherein the photobleachable compound is selected from a compound of the general formula (3):

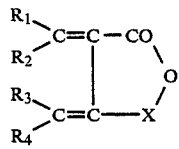 (3)

wherein X represents

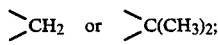

and
$R_1$, $R_2$ and $R_4$ independently represent a group selected from hydrogen, alkyl or aryl (including substituted aryl), with the proviso that one of $R_1$ and $R_2$ is always hydrogen, and $R_3$ is a 3-thienyl, 3-furyl, 3-benzothienyl or 3-benzofuryl group in which the 2-position is substituted with an alkyl, aralkyl or aryl group (including substituted aryl).

4. A process according to claim 2 in which the substrate is a semi-conductor wafer.

5. A process according to claim 4 in which the photochromic compound in the CEL is converted to its coloured form by exposure to activating radiation prior to the imaging step.

6. A process according to claim 4 in which the photoresist is a positive photoresist comprising a novolac resin and a photosensitive cross-linking agent.

7. A process according to claim 3 in which the photoresist bearing the CEL layer is subjected to a baking step prior to exposing said photoresist in step (c) to convert the photochromic compound to its colored form.

8. A process according to claim 6 in which the CEL layer is formed by deposition from a solution of the photobleachable compound in a novolac resin composition.

9. In a process for producing a developed photoresist having improved resolution by photolithography wherein a photoresist layer is formed on a substrate, a contrast enhancing layer (CEL) is deposited directly on the photoresist layer and is rendered optically opaque by incorporation of a photobleachable, coloured compound and the photoresist is exposed through an imaging pattern and through the CEL using radiation which is effective to bleach said compound, the improvement consisting essentially of selecting as the photobleachable compound a reversible photochromic compound of the general formula (1):

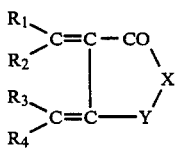 (1)

wherein Y represents

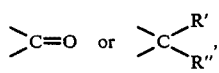

R' and R" being hydrogen or alkyl;
X represents oxygen or

in which A is hydrogen or an alkyl or aryl group;
$R_1$, $R_2$, $R_3$ and $R_4$ represent aryl, alkyl, aralkyl, hydrogen or heterocyclic groups; and
developing the photoresist and removing the CEL simultaneously in a single step using a developer in which both the CEL and the unexposed parts of the photoresist are soluble.

10. A process according to claim 9 in which the developer is an aqueous alkali.

11. A process according to claim 10 in which the photoresist is a positive photoresist comprising a novolac resin and a photosensitive cross-linking agent.

12. A process for producing a developed photoresist having improved resolution by photolithography wherein:
 (a) a positive photoresist layer is formed on a substrate;
 (b) a contrast enhancing layer (CEL) is formed directly on a photoresist layer by applying to said photoresist layer a solution or dispersion of a photobleachable compound in a solvent followed by drying to produce a superficial layer of a CEL in direct contact with said photoresist;

(c) the photoresist is exposed through an imaging pattern and through the CEL using radiation which is effective to bleach said compound, the improvement consisting essentially of selecting as the photobleachable compound, a reversible photochromic compound of the general formula (2) below:

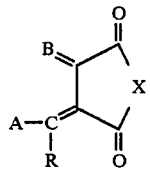 (2)

wherein X represents oxygen or

in which A is hydrogen or an alkyl or aryl group;
R represents an alkyl, aryl, aralkyl or heterocyclic group;
A represents a furyl, thienyl, benzofuryl or benzothienyl group;
B represents an adamantylidene group or the grouping:

wherein $R_6$ and $R_7$ independently represents an alkyl, aryl, aralkyl or heterocyclic group or one of $R_6$ and $R_7$ represents hydrogen and the other represents an alkyl, aryl, aralkyl or heterocyclic group, and developing the photoresist and removing the CEL simultaneously in a single step using a developer in which both the CEL and the unexposed parts of the photoresist are soluble.

13. A process for producing a developed photoresist having improved resolution by photolithography using a contrast enhancing layer (CEL), wherein the development of the photoresist and the removal of the CEL is carried out as a single step, said process consisting essentially of:

(a) forming a photoresist layer on a substrate;
(b) forming a contrast enhancing layer (CEL) directly on the photoresist layer by applying to said photoresist layer a solution or dispersion of a photobleachable compound in a solvent, followed by drying to produce a superficial layer of an opaque CEL in direct contact with said photoresist;
(c) exposing the photoresist through an imaging pattern and through the CEL using radiation which is effective to bleach said compound and simultaneously removing the CEL; and
(d) simultaneously developing the photoresist and removing the CEL using an alkali developer in a single step, wherein the photobleachable compound is selected from a compound of the general formula (3) below:

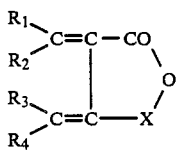 (3)

wherein X represents

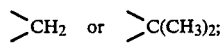

$R_1$, $R_2$ and $R_4$ independently represents a group selected from hydrogen, alkyl or aryl, including substituted aryl, with the proviso that one of $R_1$ and $R_2$ is always hydrogen, and $R_3$ is a 3-thienyl, 3-furyl, 3-benzothienyl or 3-benofuryl group in which the 2-position is substituted with an alkyl, aralkyl or aryl group, including substituted aryl.

14. A process according to claim 12 in which the substrate is a semi-conductor wafer.

15. A process according to claim 14 in which the photochromic compound in the CEL is converted to its coloured form by exposure to activating radiation prior to the imaging step.

16. A process according to claim 13 in which the photoresist is a positive photoresist comprising a novolac resin and a photosensitive cross-linking agent.

17. A process according to claim 13 in which the photoresist bearing the CEL layer is subjected to a baking step prior to exposing said photoresist in step (c) to convert the photochromic compound to its coloured form.

18. A process according to claim 16 in which the CEL layer is formed by deposition from a solution of the photobleachable compound in a novolac resin composition.

* * * * *